US009674642B2

(12) United States Patent
Singh et al.

(10) Patent No.: US 9,674,642 B2
(45) Date of Patent: Jun. 6, 2017

(54) METHOD AND SYSTEM FOR REAL-TIME MONITORING OF OPERATING CONDITION AT AN INFRASTRUCTURE

(71) Applicant: Wipro Limited, Bangalore (IN)

(72) Inventors: Puneet Singh, Bangalore (IN); Sunil Bhat, Bangalore (IN)

(73) Assignee: WIPRO LIMITED, Bangalore (IN)

( * ) Notice: Subject to any disclaimer, the term of this patent is extended or adjusted under 35 U.S.C. 154(b) by 0 days.

(21) Appl. No.: 14/928,067

(22) Filed: Oct. 30, 2015

(65) Prior Publication Data
US 2017/0061767 A1   Mar. 2, 2017

(30) Foreign Application Priority Data
Aug. 24, 2015   (IN) .......................... 4425/CHE/2015

(51) Int. Cl.
*G08B 1/08* (2006.01)
*H04W 4/00* (2009.01)
(Continued)

(52) U.S. Cl.
CPC ............. *H04W 4/006* (2013.01); *G01M 5/00* (2013.01); *H04W 88/04* (2013.01)

(58) Field of Classification Search
CPC ... G08B 21/0461; H04W 4/006; H04W 88/04
(Continued)

(56) References Cited

U.S. PATENT DOCUMENTS 5,461,365 A   10/1995  Schlager et al.
8,396,485 B2   3/2013  Grainger et al.
(Continued)

FOREIGN PATENT DOCUMENTS

WO   WO 2004/112411 A1   12/2004

OTHER PUBLICATIONS

Audrey Presley, "TimeForge Demos 'PlaceForge,' a BLE Beacon Staff Tracking and Asset Management Solution, at RetailNOW Expo", available at http://www.prweb.com/releases/2014/08/prweb12067383.htm, 3 pages, Aug. 3, 2014.
(Continued)

*Primary Examiner* — Jack K Wang
(74) *Attorney, Agent, or Firm* — Finnegan, Henderson, Farabow, Garrett & Dunner LLP

(57) ABSTRACT

The present disclosure relates to a method and system for real-time monitoring of operating condition at an infrastructure. The method comprises receiving data from one or more sensors wherein the data is associated with monitoring parameters of the infrastructure like environment condition, operator health condition and working condition of the infrastructure. The data is received by one or more mobile devices associated with one or more operators of the infrastructure. Based on the received data, the each of the mobile devices detects status of the operating condition of the infrastructure. The status is either safe or unsafe. The mobile device receives input from each of the one or more operators if there is any modification in the detected status. Based on the received input the detected status is updated. The mobile device provides one or more measures associated with the one or more monitoring parameters based on the updated status.

18 Claims, 6 Drawing Sheets

(51) Int. Cl.
   *G01M 5/00*   (2006.01)
   *H04N 7/18*   (2006.01)
   *G01B 5/28*   (2006.01)
   *G06K 9/00*   (2006.01)
   *H04W 88/04*  (2009.01)

(58) Field of Classification Search
   USPC .................................................. 340/539.11
   See application file for complete search history.

(56) References Cited

U.S. PATENT DOCUMENTS

| | | | |
|---|---|---|---|
| 2007/0260375 A1 | 11/2007 | Hilton | |
| 2010/0064241 A1* | 3/2010 | Tays | G06Q 10/06 |
| | | | 715/771 |
| 2010/0115093 A1* | 5/2010 | Rice | H04L 12/24 |
| | | | 709/224 |
| 2011/0308638 A1* | 12/2011 | Hyland | E03B 9/06 |
| | | | 137/299 |
| 2012/0290225 A1 | 11/2012 | Julian et al. | |
| 2014/0132411 A1 | 5/2014 | Buchheim et al. | |
| 2014/0156472 A1 | 6/2014 | Stuntebeck et al. | |
| 2014/0191868 A1 | 7/2014 | Ortiz et al. | |
| 2014/0214500 A1 | 7/2014 | Hudson et al. | |
| 2015/0287302 A1* | 10/2015 | Ruess | G08B 13/19656 |
| | | | 348/143 |
| 2016/0217669 A1* | 7/2016 | Benoit | G08B 25/009 |
| 2016/0335686 A1* | 11/2016 | AthuluruTlrumala | G06Q 30/0613 |

OTHER PUBLICATIONS

Extended European Search Report issued from the European Patent Office for Application No. 16153513.3—1557; mailed Jan. 20, 2017 (7 pgs.).

* cited by examiner

METHOD AND SYSTEM FOR REAL-TIME MONITORING OF OPERATING CONDITION AT AN INFRASTRUCTURE

TECHNICAL FIELD

The present subject matter is related, in general to infrastructure monitoring, and more particularly, but not exclusively to a method and system for real-time monitoring of operating condition at an infrastructure.

BACKGROUND

The maintenance of infrastructure for example buildings is carried out by operators in remote or hazardous environment, with significant risks and chances of fatalities of the operators while working at the infrastructure. The safety of the operators and also safety of the infrastructure is ascertained by the decision makers who are usually at some distance from the operators of the infrastructure.

At present the solution for assessing risk of an accident, fatality or infrastructure failure is based on manual monitoring and periodic maintenance of the infrastructure. But there are few problems associated with this solution. As an example, the operator may not assess the conditions at the infrastructure properly or the operator may take decision based on his past experience. The misjudgment of the operator may cause disasters and fatalities. In such cases, quick information about the situation and the correct assessment of the situation by the decision makers to respond becomes an essential element for saving the operators and the infrastructure. Further due to incorrect, insufficient, or information solely based on past experience of the operators, one or more components of infrastructure may breakdown which may not have been observed by the decision makers or the operators. And due to the breakdown of the infrastructure, there shall be stoppage of work which leads to reduction in productivity.

The issue mainly faced in infrastructure monitoring is to provide the information of the operating condition in real time. Also, to provide clear and correct inputs for the decision makers to take quick actions for reducing the risk of an accident or fatality of operators at the infrastructure.

SUMMARY

Disclosed herein is a method and system for real-time monitoring of operating condition at an infrastructure. One or more operators at the infrastructure are provided with a mobile device wherein the mobile device is configured with operating condition determination application. The mobile device receives sensor data from one or more sensors configured at the infrastructure. The one or more sensors are configured to provide data associated with monitoring parameters of the infrastructure to the mobile device. The mobile device detects status of the operating condition at the infrastructure based on the received data. The status is either safe or unsafe. The mobile device updates the status based on input received on validity of the status by the one or more operators. The one or more measures associated with the one or more monitoring parameters are provided based on the updated status.

Accordingly, the present disclosure relates to a method for real-time monitoring of operating condition at an infrastructure. The method comprises receiving, by one or more mobile devices associated with one or more operators of the infrastructure, data related to one or more monitoring parameters from one or more sensors. Based on the data, the status of the operating condition at the infrastructure wherein the status is at least one of safe and unsafe. The method further comprises updating the status based on input received on validity of the status from the one or more operators. Based on the updated status, one or more measures associated with the one or more monitoring parameters are provided for monitoring the operating condition at the infrastructure.

Further, the present disclosure relates to a mobile device for real-time monitoring of operating condition at an infrastructure. The mobile device comprises a processor and a memory communicatively coupled to the processor, wherein the memory stores processor-executable instructions, which, on execution, causes the processor to receive data related to one or more monitoring parameters from one or more sensors. The instructions cause the processor to detect status of the operating condition at the infrastructure based on the data, wherein the status is at least one of safe and unsafe. Thereafter, the processor updates the status based on input received on validity of the status from the one or more operator. Further, the processor provides one or more measures associated with the one or more monitoring parameters based on the updated status thereby monitoring the operating condition at the infrastructure.

Furthermore, the present disclosure relates to a non-transitory computer readable medium including instructions stored thereon that when processed by at least one processor cause a mobile device to perform the acts of receiving data related to one or more monitoring parameters from one or more sensors. Upon receiving the data, the mobile device detects status of the operating condition at the infrastructure, wherein the status is at least one of safe and unsafe. Thereafter, the mobile device updates the status based on input received on validity of the status from the one or more operators. The mobile device provides one or more measures associated with the one or more monitoring parameters based on the updated status thereby monitoring the operating condition at the infrastructure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE ACCOMPANYING DRAWINGS

The accompanying drawings, which are incorporated in and constitute a part of this disclosure, illustrate exemplary embodiments and, together with the description, serve to explain the disclosed principles. In the figures, the left-most digit(s) of a reference number identifies the figure in which the reference number first appears. The same numbers are used throughout the figures to reference like features and components. Some embodiments of system and/or methods in accordance with embodiments of the present subject matter are now described, by way of example only, and with reference to the accompanying figures, in which:

Figure 1A:
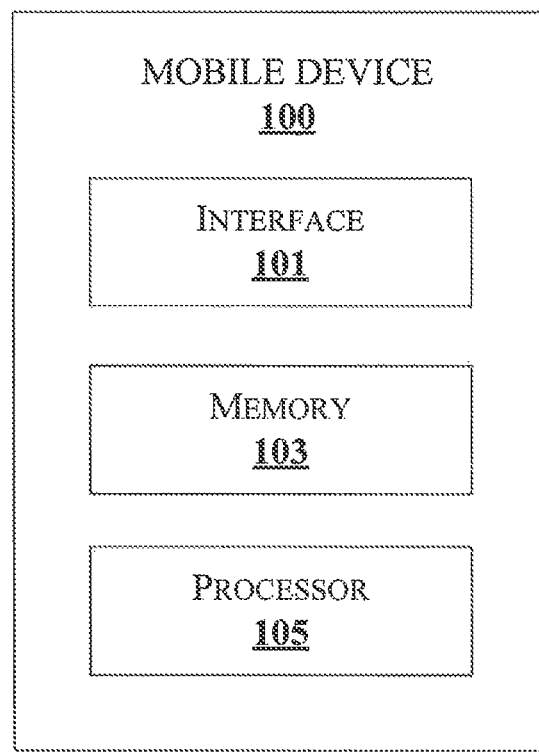
FIG. 1a shows a block diagram illustrating a mobile device for real-time monitoring of operating condition at an infrastructure in accordance with some embodiments of the present disclosure.

It should be appreciated by those skilled in the art that any block diagrams herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and executed by a computer or processor, whether or not such computer or processor is explicitly shown.

DETAILED DESCRIPTION

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described in detail below. It should be understood, however that it is not intended to limit the disclosure to the particular forms disclosed, but on the contrary, the disclosure is to cover all modifications, equivalents, and alternative falling within the spirit and the scope of the disclosure.

The terms "comprises", "comprising", or any other variations thereof, are intended to cover a non-exclusive inclusion, such that a setup, device or method that comprises a list of components or steps does not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or method.

The present disclosure relates to a method and system for real-time monitoring of operating condition at an infrastructure. The infrastructure may include but not limited to buildings, equipments and assets. The operating condition refers to working conditions for operators at the infrastructure. The operating condition may also refer to working condition of the infrastructure itself. The system comprises of one or more sensors, one or more mobile devices and an infrastructure monitoring server. The one or more sensors are configured at the infrastructure. The one more sensors are configured to monitor one or more parameters of the infrastructure. The one or more sensors may include but not limited to a health monitoring sensor for monitoring health condition of the operator at the infrastructure, an infrastructure monitoring sensor for monitoring operating condition of the infrastructure and environment sensor for monitoring environmental conditions of the infrastructure. The one or more sensors transmit data associated with the monitoring parameters of the infrastructure to each of the one or more mobile devices over a communication network. Based on the data, each of the one or more mobile devices detects whether the status is safe or unsafe for the working of the operators at the infrastructure. The validity of the detected status is provided by the one or more operators and based on inputs from the one or more operators on the validity, the status is updated. Based on the updated status, one or more measures are provided by the mobile devices to avoid the risk or fatality of the operators.

In the following detailed description of the embodiments of the disclosure, reference is made to the accompanying drawings that form a part hereof, and in which are shown by way of illustration specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

FIG. 1a shows a block diagram illustrating a mobile device 100 in accordance with some embodiments of the present disclosure.

The mobile device 100 comprises an interface 101, a memory 103 and a processor 105. As an example, the mobile device 100 may include, but not limited to, a mobile phone and a tablet computer. The interface 101 and the memory 103 are communicatively coupled to the processor 105. The memory 103 stores processor-executable instructions which on execution cause the processor 105 to perform one or more steps. In an embodiment, the mobile device 100 is associated with an operator working at the infrastructure for monitoring and periodic maintenance of the infrastructure. The infrastructure may include, but not limited to, buildings, equipments and assets. As an example, the operator may be a ground staff of the infrastructure.

In an embodiment, the interface 101 is used to receive data related to one or more monitoring parameters from one or more sensors over a communication network. As an example, the communication network may include, but not limited to, a wired network, a wireless network and a combination thereof. In an embodiment, the one or more sensors are configured at the infrastructure. The one or more sensors may include, but not limited to, health monitoring sensor for monitoring health condition of the one or more operators, infrastructure monitoring sensor for monitoring operating condition of the infrastructure and environment sensor for monitoring environmental conditions of the infrastructure. As an example, the health monitoring sensor may include, but not limited to, Electrocardiogram (ECG) monitoring sensor and blood pressure sensor, the infrastructure monitoring sensor may include, but not limited to, altitude sensor, gyroscopes, pressure sensor, accelerometer and the environment sensor may include, but not limited to, temperature sensor, wind speed sensor and humidity sensor.

In another embodiment, the interface 101 may receive the data related to one or more monitoring parameters from a client device (not shown in FIG. 1a). The client device is configured at the infrastructure and is connected to the one or more sensors. As an example, the client device may be a computing device capable of receiving the data from the one or more sensors and transmitting the data over a communication network. The one or more sensors provide the data associated with the one or more monitoring parameters to the client device. The client device provides the data to the mobile device 100 over the communication network.

The processor 105 receives the data and detects whether the operating condition is safe or unsafe for the one or more operators and also for the infrastructure based on the received data. The processor 105 obtains a sensor value from the received data and compares the sensor value with predefined sensor value to determine the status as safe or unsafe. The predefined sensor value is obtained from an infrastructure monitoring server (not shown in FIG. 1). The infrastructure monitoring server is configured for remote monitoring of the operating condition at the infrastructure. The infrastructure monitoring server generates predefined sensor value based on past experience of the operators to determine whether the operating condition is safe or unsafe. The processor 105 also receives input from the one or more operators on validity of the detected status i.e whether the detected status is correct or wrong. If the one or more operators determine that the detected status is wrong then the processor 105 changes the status and updates the actual status based on the input received from the operator. As an example, the status detected by the processor 105 based on the received data may be safe. The operator working at the infrastructure may feel that the environment condition is not suitable for working and hence it may affect the health of the operator i.e the operator determining the actual status to be unsafe. Therefore, the operator may provide an input to change the status. Based on the input from the operator, the processor 105 updates the status of the operating condition. The operator also provides input associated with the monitoring parameter i.e the "environment condition" in this scenario affecting the status of the operating condition. The input associated with the monitoring parameter is provided to the infrastructure monitoring server. The infrastructure monitoring server updates the predefined sensor value based on the monitoring parameter.

In an embodiment, the processor 105 provides one or more measures to be carried out in order to avoid the risk involved for the operator while working at the infrastructure. The one or more measures are based on the updated status of the operating condition at the infrastructure. As an example, if the environment condition is not suitable for the operators of the infrastructure, the measures suggested by the processor 105 may be to stop the work at the infrastructure. If the operator's health condition is not fine then the measure suggested by the processor 105 may be to replace the operator or provide an indication for medical assistance. Similarly, if the infrastructure operating condition is not fine then the corrective measures are indicated by the processor 105 for correcting the infrastructure.

Figure 1B:
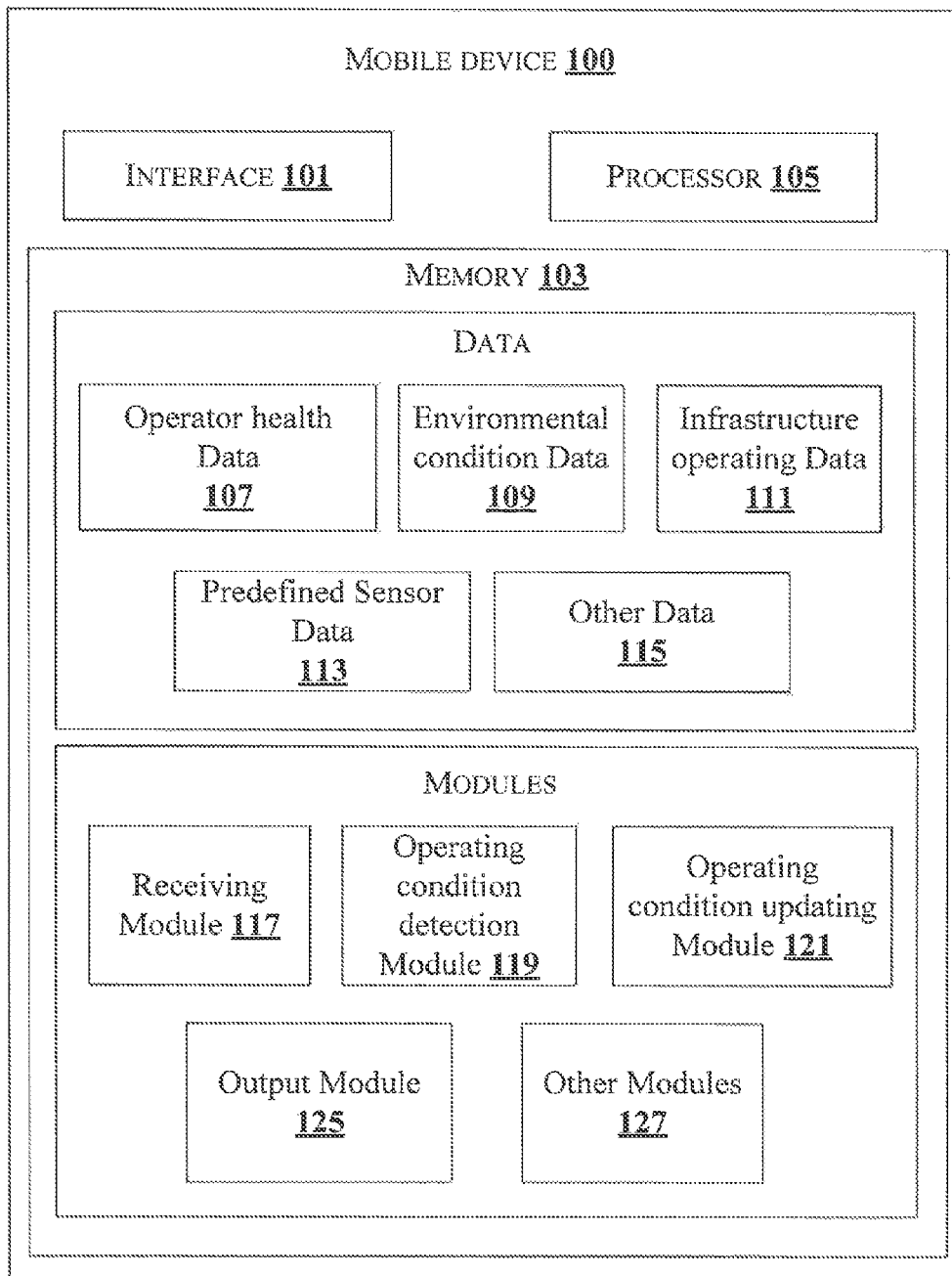
FIG. 1b shows a detailed block diagram illustrating a mobile device for real-time monitoring of operating condition at an infrastructure in accordance with some embodiments of the present disclosure.

FIG. 1b shows a detailed block diagram illustrating a mobile device 100 in accordance with some embodiments of the present disclosure.

In one implementation, the mobile device 100 receives input data from one or more sensors. As an example, the received input data is stored within the memory 103. In an embodiment, the input data includes operator health data 107, environmental condition data 109, infrastructure operating data 111 and other data 115. The mobile device 100 also receives predefined sensor data 113 from the infrastructure monitoring sensor (not shown in FIG. 1b). In the illustrated FIG. 1b, one or more modules stored in the memory 103 are described herein in detail.

In one embodiment, the input data may be stored in the memory 103 in the form of various data structures. Additionally, the aforementioned data can be organized using data models, such as relational or hierarchical data models.

The other data 115 may store data, including temporary data and temporary files, generated by modules for performing the various functions of the mobile device 100.

In an embodiment, the operator health data 107 is received from the health monitoring sensor configured at the infrastructure. The health monitoring sensor is associated with each of the one or more operators at the infrastructure. The health monitoring sensor monitors the health condition of the operators. The health monitoring sensor may include, but not limited to, an ECG sensor or blood pressure sensor. The health monitoring sensor measures the health condition of the operator and provides the data to each of the one or more mobile devices 100 through the communication network.

In an embodiment, the environmental condition data 109 is received from environment sensor configured at the infrastructure. The environment sensor is configured to measure the environmental conditions at the infrastructure. The environmental conditions may include but not limited to wind speed, temperature and foul smell. The environment sensor measures the environmental conditions and provides the environmental condition data 109 to each of the one or more mobile devices 100 through the communication network.

In an embodiment, the infrastructure operating data 111 is received from the infrastructure operating sensor. The infrastructure operating sensor is configured at the infrastructure for monitoring operating conditions of the infrastructure. As an example, the operating conditions of the infrastructure monitored may include, but not limited to, altitude of the infrastructure, angle of inclination of the infrastructure and speed. Upon detecting the conditions in real-time, the infrastructure monitoring sensor provides the data associated with the condition of the infrastructure to each of the one or more mobile devices 100 through the communication network.

In an embodiment, the predefined sensor data 113 is received from the infrastructure monitoring server. The infrastructure monitoring server is connected over a communication network to each of the one or more mobile devices 100. The infrastructure monitoring server provides the predefined sensor data 113 to each of the one or more mobile devices 100. The predefined sensor data 113 includes predefined sensor values for each of the sensor configured at the infrastructure and an aggregated sensor value based on the average value of all the predefined sensor value.

In an embodiment, the data stored in the memory 103 are processed by the modules of the mobile device 100. The modules may be stored within the memory 103 as shown in FIG. 1b. In an example, the modules, communicatively coupled to the processor 105, may also be present outside the memory 103. As used herein, the term module refers to an application specific integrated circuit (ASIC), an electronic circuit, a hardware processor 105 (shared, dedicated, or group) and memory 103 that execute one or more software or firmware programs, a combinational logic circuit, and/or other suitable components that provide the described functionality.

In one implementation, the modules may include, for example, a receiving module 117, operating condition detection module 119, operating condition updating module 121, output module 125 and other modules 127. The other modules 127 may be used to perform various miscellaneous functionalities of the mobile device 100. It will be appreciated that such aforementioned modules may be represented as a single module or a combination of different modules.

In an embodiment, the receiving module 117 is configured to receive data from the one or more sensors. The data is associated with one or more monitoring parameters of the infrastructure. The monitoring parameters are operator's health condition, infrastructure operating condition and environmental condition. The sensors are configured at the infrastructure for continuously monitoring the monitoring parameters and providing the data to each of the one or more mobile devices 100.

In an embodiment, the operating condition detection module 119 is configured to detect the status of the operating condition of the infrastructure. The operating condition detection module 119 detects the status as either safe or unsafe based on the received data. The operating condition detection module 119 obtains the sensor value from the received data and compares the sensor value with the predefined sensor value. If the sensor value exceeds the predefined sensor value then the status is detected as unsafe. If the sensor value is within the predefined sensor value then the status is detected as safe. Each of the mobile devices 100 displays the status of the operating condition using the output module 125.

In an embodiment, the operating condition updating module 121 is configured to update the status of the operating condition based on the detected status. The one or more operators may update the status if the detected status is wrong. For example, the operating condition detection module 119 may detect the status of the operating condition to be safe. But the operator may feel that the environment condition is not suitable for working at the infrastructure as the temperature is very high. In this scenario, the operator may provide an input to the mobile device 100 to change the status as unsafe from safe. Upon providing the input, the mobile device 100 also requests the operator to indicate the monitoring parameter affecting the operating condition of the infrastructure. Based on the input, the operating condition updating module 121 updates the status and transmits the data associated with the updated status to the infrastructure monitoring server. The operating condition updating module 121 also transmits information associated with the monitoring parameter affecting the operating condition to the infrastructure monitoring server. The infrastructure monitoring server updates the status and also updates the predefined sensor value based on the monitoring parameter and provides the updated data to each of the one or more mobile devices 100 over a communication network. The updated predefined value is used by each of the one or more mobile devices 100 for comparing with the sensor value obtained from the one or more sensors.

In an embodiment, the output module 125 is configured to display the status of the operating condition in the mobile device 100.

Figure 2A:
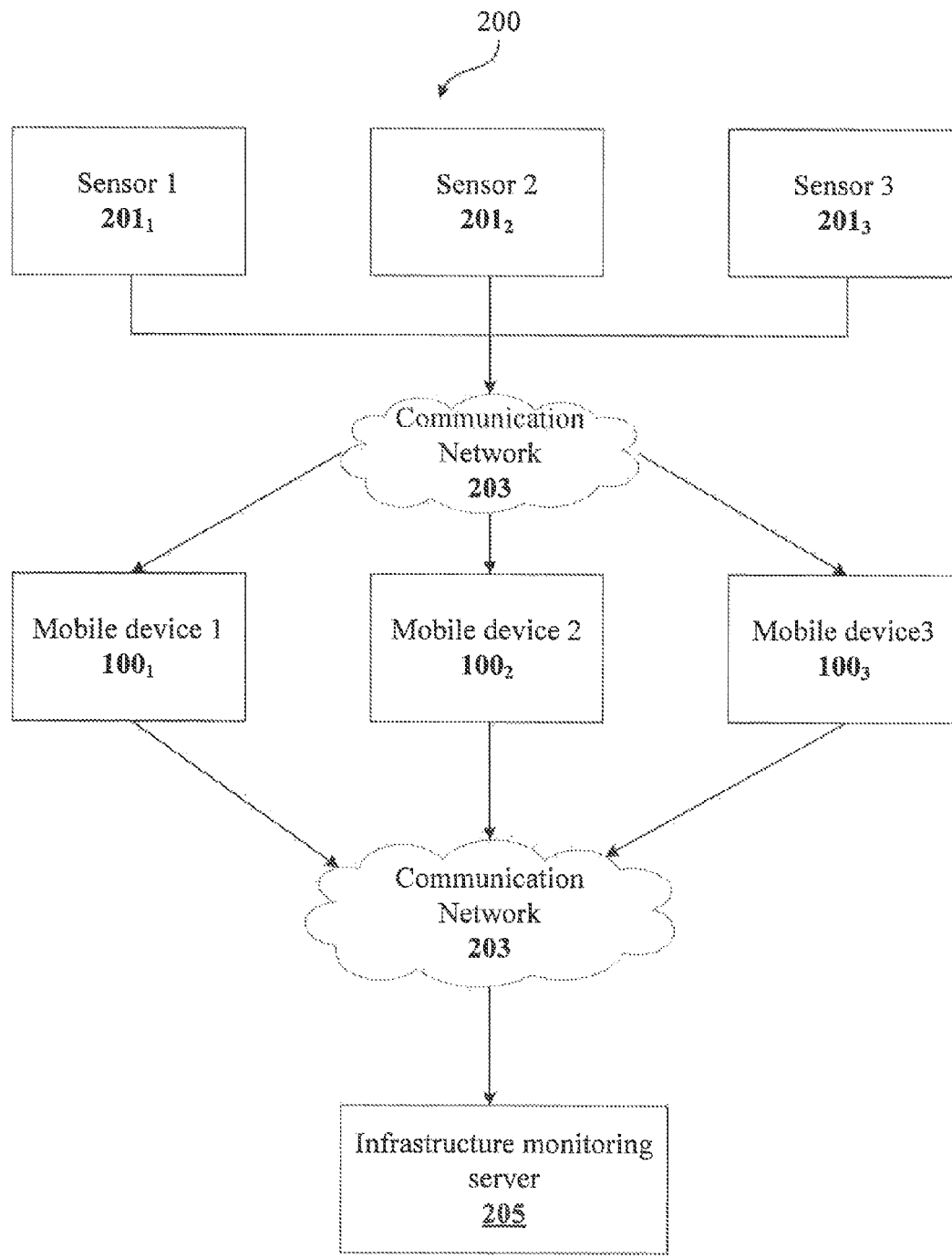
FIG. 2a shows a block diagram illustrating an exemplary environment for real-time monitoring of operating condition at an infrastructure in accordance with some embodiments of the present disclosure.

FIG. 2a shows a block diagram illustrating an exemplary environment 200 for real-time monitoring of operating condition at an infrastructure in accordance with some embodiments of the present disclosure.

Figure 2B:
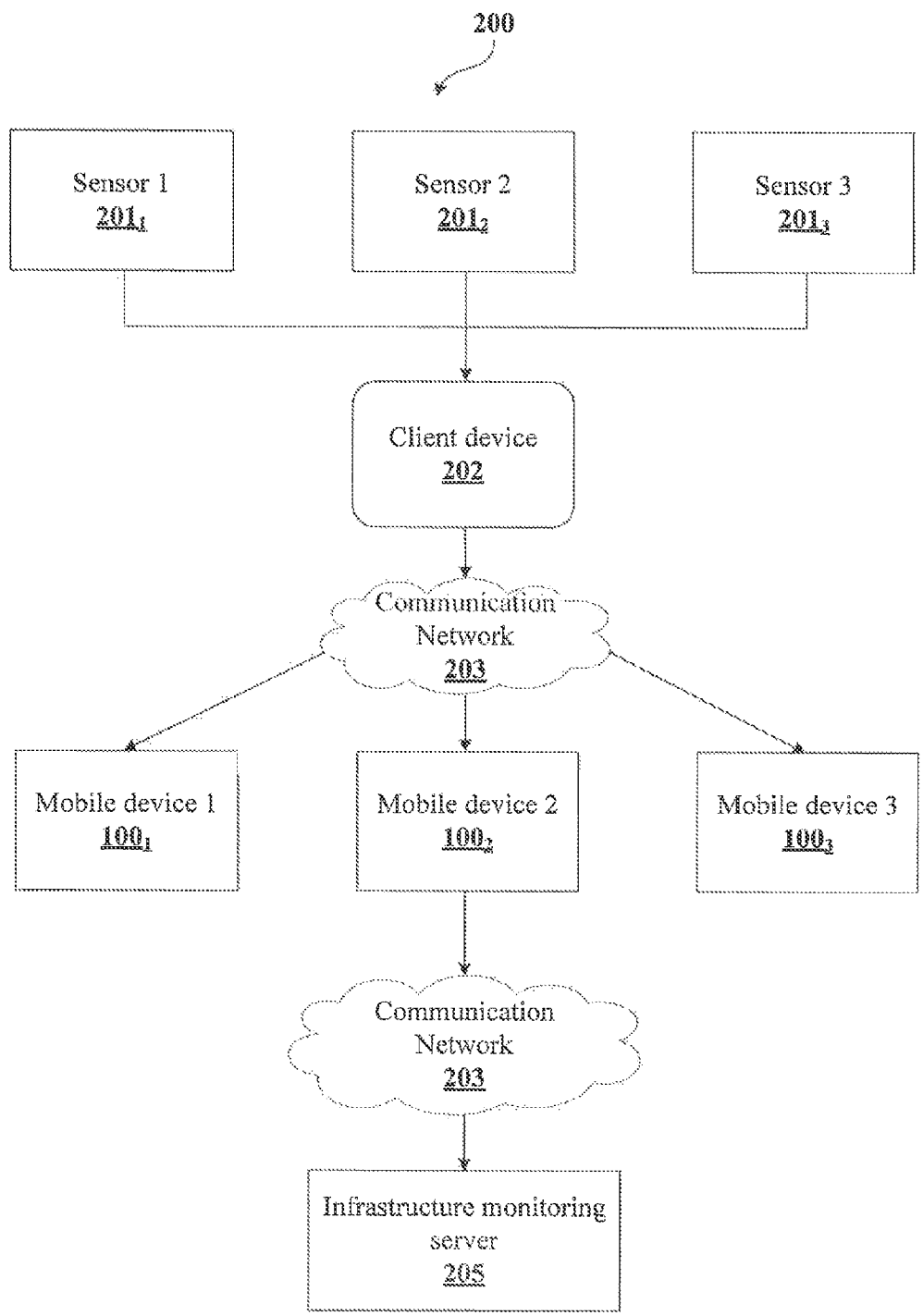
FIG. 2b shows a block diagram illustrating an exemplary environment for real-time monitoring of operating condition at an infrastructure in accordance with some embodiments of the present disclosure.

In an exemplary embodiment as illustrated in FIG. 2a, the one or more sensors (collectively referred as sensors 201) namely, sensor 1 $201_1$, sensor 2 $201_2$ and sensor 3 $201_3$ are configured at the infrastructure. The sensor 1 $201_1$ is for monitoring operator's health condition. The sensor 2 $201_2$ is for monitoring environmental conditions at the infrastructure and sensor 3 $201_3$ is for monitoring operating condition of the infrastructure. As an example, three operators namely a first operator, a second operator and a third operator are working at the infrastructure, wherein each operator is associated with a mobile device 100. The mobile device 1 $100_1$ is associated with the first operator. The mobile device 2 $100_2$ is associated with the second operator and the mobile device 3 $100_3$ is associated with the third operator. In an embodiment, each of the mobile devices 100 is connected to the infrastructure monitoring server 205 through the communication network 203. In an embodiment each mobile device 100 is configured with an application for real-time monitoring of the operating condition at the infrastructure. The infrastructure monitoring server 205 generates the predefined sensor data 113 based on past experience of the operators at the infrastructure. The predefined sensor data 113 includes predefined sensor value. As an example, the predefined sensor value may be 100. The infrastructure monitoring server 205 provides the predefined sensor value to each of the one or more mobile devices 100. Each of the sensors 201 provides the measured data to each of the one or more mobile devices 100. In an embodiment, each of the sensors 201 is associated with a client device 202 as shown in FIG. 2b. Each of the sensors 201 provides the measured data to the client device 202 and the client device 202 transmits the measured data to each of the one or more mobile devices 100 through the communication network 203. Upon receiving the measured data, each of the one or more mobile devices 100 obtains the sensor value from the measured data. As an example, the obtained sensor value is 80. The obtained sensor value is the aggregated sensor value from the sensor 1 $201_1$, sensor 2 $201_2$ and sensor 3 $201_3$. The application in each of the one or more mobile devices 100 compares the obtained sensor value with the predefined sensor value. The obtained sensor value is less than the predefined sensor value. Therefore, the application detects the status of the operating condition as safe. As an example, the first operator may feel that the environmental condition is not suitable for working at the infrastructure because of high temperature and therefore changes the status. The first operator provides the input to the application to change the status. The second and the third operator may feel that the environmental conditions are safe to work at the infrastructure. Even if one of the one or more operators wishes to change the status, the operator may do so using the application in the mobile device 100. Therefore, based on the input from the first operator, the status is changed from safe to unsafe. The first operator also indicates the monitoring parameter affecting the status. In this scenario, the monitoring parameter affecting the operating condition is environmental condition. The mobile device 1 $100_1$ provides the information associated with monitoring parameter to the infrastructure monitoring server 205. The infrastructure monitoring server 205 updates the predefined sensor value based on the received information. The updated predefined sensor value is provided to each of the one or more mobile devices 100.

Figure 3:
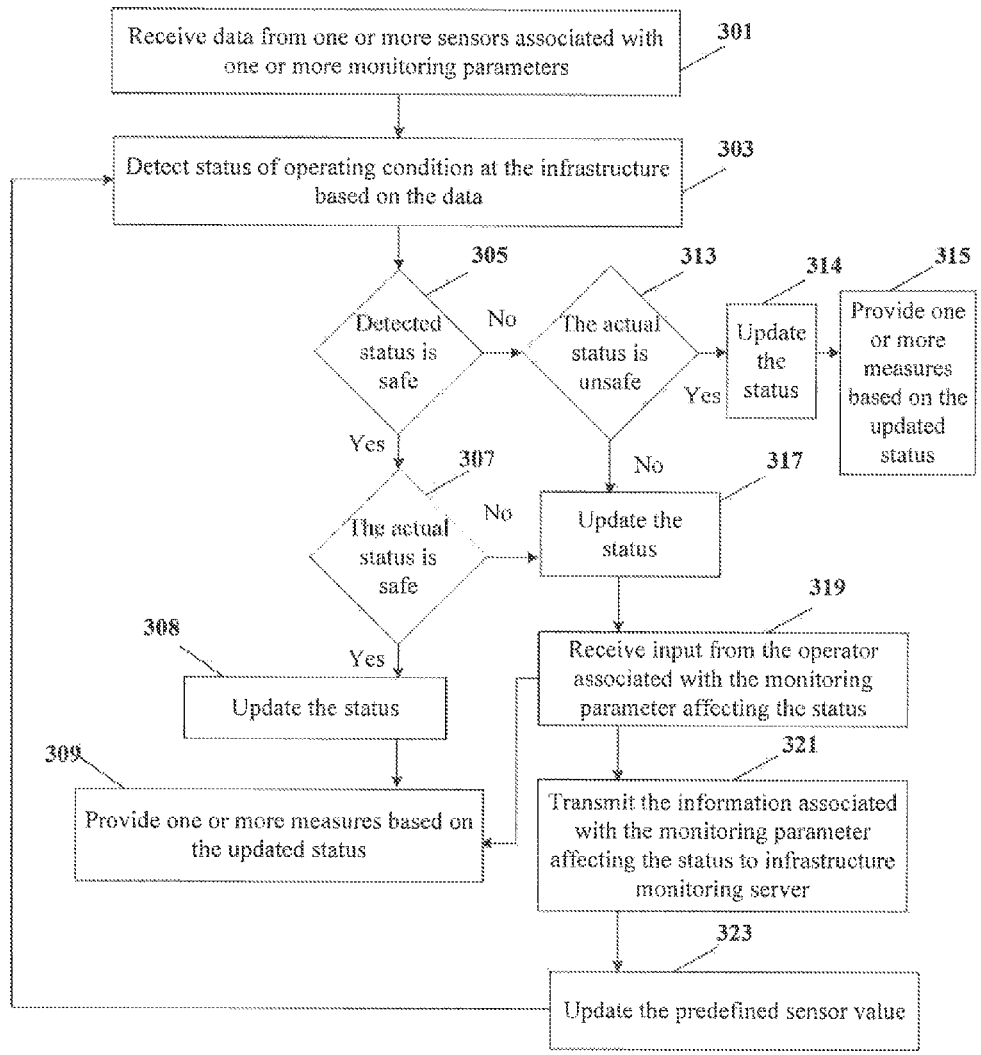
FIG. 3 illustrates a flowchart showing method for real-time monitoring of operating condition at an infrastructure in accordance with some embodiments of the present disclosure.

FIG. 3 illustrates a flowchart showing method for real-time monitoring of operating condition at an infrastructure in accordance with some embodiments of the present disclosure.

As illustrated in FIG. 3, the method 300 comprises one or more blocks for real-time monitoring of operating condition at an infrastructure using one or more mobile devices 100. The method 300 may be described in the general context of computer executable instructions. Generally, computer executable instructions can include routines, programs, objects, components, data structures, procedures, modules, and functions, which perform particular functions or implement particular abstract data types.

The order in which the method 300 is described is not intended to be construed as a limitation, and any number of the described method blocks can be combined in any order to implement the method. Additionally, individual blocks may be deleted from the methods without departing from the spirit and scope of the subject matter described herein. Furthermore, the method can be implemented in any suitable hardware, software, firmware, or combination thereof.

At block 301, input data of one or more monitoring parameters are received from one or more sensors. In an embodiment, the one or more sensors are configured at the infrastructure. The one or more sensors may include, but not limited to, health monitoring sensor, environmental condition monitoring sensor and infrastructure monitoring sensor. The sensors measure the monitored parameters in real-time and provide the measured data to each of the mobile devices 100 associated with the operators of the infrastructure.

At block 303, status of the operating condition is detected. In an embodiment, each mobile device 100 is configured with an application for real-time monitoring of the operating condition at the infrastructure. Each of the one or more mobile devices 100 associated with the one or more operators receives the measured data. The application obtains the sensor value from the measured data and compares the sensor value with predefined sensor value. The predefined sensor value is obtained from an infrastructure monitoring server. The infrastructure monitoring server is connected to each of the one or more mobile devices 100 through a communication network. The application detects the operating condition as safe if the obtained sensor value is less than the predefined sensor value. The application detects the operating condition as unsafe if the obtained sensor value exceeds the predefined sensor value.

At block 305, the detected status is determined as whether safe or unsafe. In an embodiment, if the status detected by the application in the mobile device 100 is safe then the method proceed to block 307 via "Yes". If the status detected by the application is unsafe, then the method proceeds to block 313 via "No".

At block 307, the detected status is validated by the one or more operator's i.e the operators verify whether the detected status is correct or wrong. In an embodiment, if the actual status detected by the operator is safe then the method proceeds to block 308 via "Yes". Since the detected status and the actual status both are safe, the status is updated as safe at block 308. At block 309, one or more measures are provided by the mobile device 100 based on the updated status. The measure provided in this scenario may be to continue the work.

If the operator detects the actual status as unsafe then the method proceeds to block 317 via "No". The actual status may be detected as unsafe based on the monitoring parameter. Since the actual status is determined as "unsafe" by the operator, the status is updated as unsafe at block 317 and the method proceeds to block 319. Therefore, one or more measures are provided by the mobile device 100 based on the updated status at block 309. As an example, the monitoring parameter affecting the status may be the operator's health condition. Therefore, the measure provided by the mobile device 100 may to stop the work or provide information to the medical health care for assistance.

At block 319, the input associated with the monitoring parameter affecting the operating condition is provided by the operator. The mobile device 100 receives the input and transmits the input to the infrastructure monitoring server at block 321.

At block 323, the predefined value is updated. The infrastructure monitoring server updates the predefined sensor value. The predefined sensor value is updated based on the input received from the mobile device 100 on the monitoring parameter affecting the operating condition. The updated predefined sensor value is provided to the mobile device 100 for future monitoring.

At block 313, the detected status is validated by the one or more operator's i.e the operators verify whether the detected status is correct or wrong. In an embodiment, if the actual status detected by the operator is unsafe, then the method proceeds to block 315. Since the actual status and the detected status both are unsafe, the status is updated at block 314 as unsafe. At block 314, one or more measures are provided by the mobile device 100 based on the updated status. The measure provided in this scenario may be to stop the work. In an embodiment, if the actual status detected by the operator is safe, then the method proceeds to block 319.

Computer System

Figure 4:
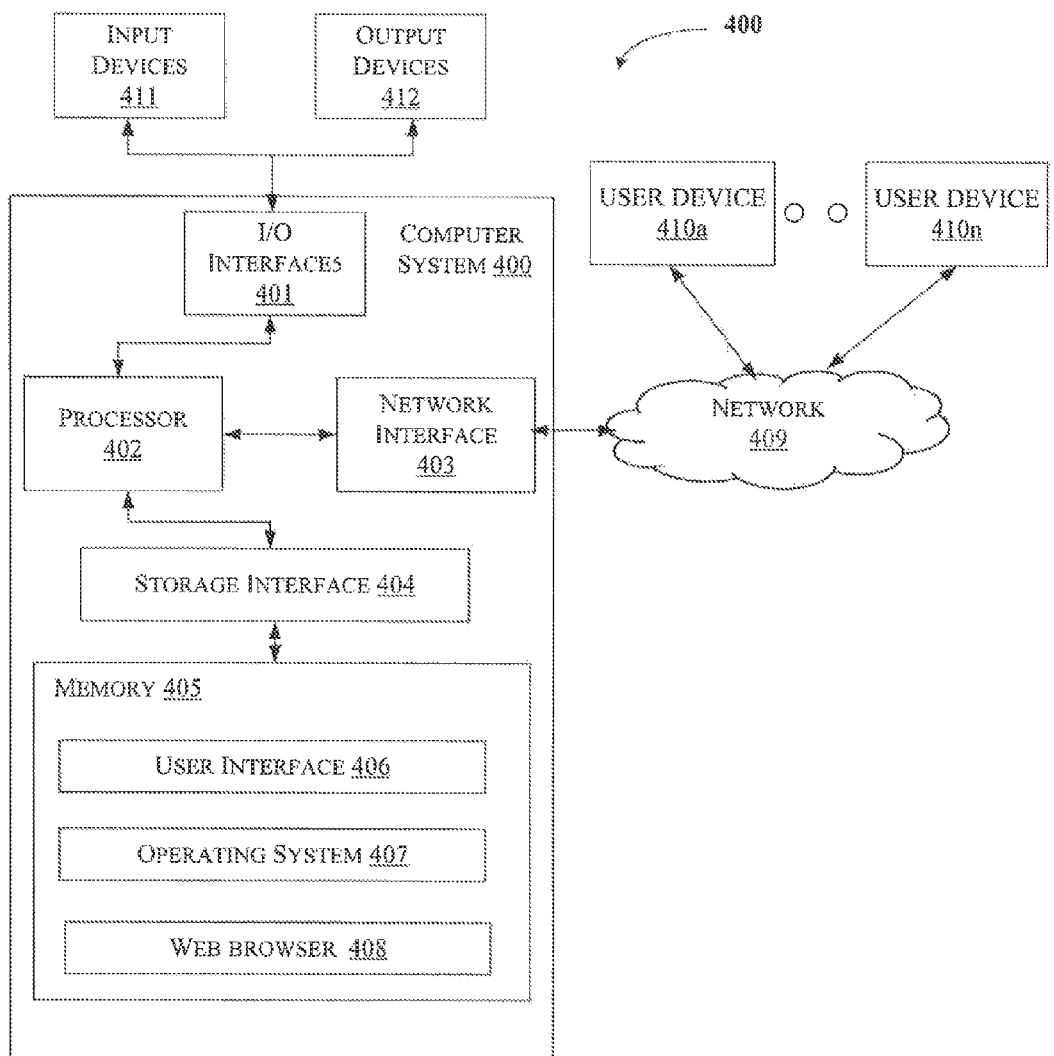
FIG. 4 illustrates a block diagram of an exemplary computer system for implementing embodiments consistent with the present disclosure.

FIG. 4 illustrates a block diagram of an exemplary computer system 400 for implementing embodiments consistent with the present invention. In an embodiment, the computer system 400 is used to provide real-time monitoring of operating condition at an infrastructure using the mobile device 100. The computer system 400 may comprise a central processing unit ("CPU" or "processor") 402. The processor 402 may comprise at least one data processor for executing program components for executing user- or system-generated business processes. A user may include a person, a person using a device such as such as those included in this invention, or such a device itself. The processor 402 may include specialized processing units such as integrated system (bus) controllers, memory management control units, floating point units, graphics processing units, digital signal processing units, etc.

The processor 402 may be disposed in communication with one or more input/output (I/O) devices (411 and 412) via I/O interface 401. The I/O interface 401 may employ communication protocols/methods such as, without limitation, audio, analog, digital, stereo, IEEE-1394, serial bus, Universal Serial Bus (USB), infrared, PS/2, BNC, coaxial, component, composite, Digital Visual Interface (DVI), high-definition multimedia interface (HDMI), Radio Frequency (RF) antennas, S-Video, Video Graphics Array (VGA), IEEE 802.n/b/g/n/x, Bluetooth, cellular (e.g., Code-Division Multiple Access (CDMA), High-Speed Packet Access (HSPA+), Global System For Mobile Communications (GSM), Long-Term Evolution (LTE), WiMax, or the like), etc.

Using the I/O interface 401, the computer system 400 may communicate with one or more I/O devices (411 and 412).

In some embodiments, the processor 402 may be disposed in communication with a communication network 409 via a network interface 403. The network interface 403 may communicate with the communication network 409. The network interface 403 may employ connection protocols including, without limitation, direct connect, Ethernet (e.g., twisted pair 10/100/1000 Base T), Transmission Control Protocol/Internet Protocol (TCP/IP), token ring, IEEE 802.11a/b/g/n/x, etc. Using the network interface 403 and the communication network 409, the computer system 400 may communicate with one or more user devices 410 (a, . . . , n). The communication network 409 can be implemented as one of the different types of networks, such as intranet or Local Area Network (LAN) and such within the organization. The communication network 409 may either be a dedicated network or a shared network, which represents an association of the different types of networks that use a variety of protocols, for example, Hypertext Transfer Protocol (HTTP), Transmission Control Protocol/Internet Protocol (TCP/IP), Wireless Application Protocol (WAP), etc., to communicate with each other. Further, the communication network 409 may include a variety of network devices, including routers, bridges, servers, computing devices, storage devices, etc. The one or more user devices 410 (a, . . . , n) may include, without limitation, personal computer(s), mobile devices such as cellular telephones, smartphones, tablet computers, eBook readers, laptop computers, notebooks, gaming consoles, or the like.

In some embodiments, the processor 402 may be disposed in communication with a memory 405 (e.g., RAM, ROM, etc. not shown in FIG. 4) via a storage interface 404. The storage interface 404 may connect to memory 405 including, without limitation, memory drives, removable disc drives, etc., employing connection protocols such as Serial Advanced Technology Attachment (SATA), Integrated Drive Electronics (IDE), IEEE-1394, Universal Serial Bus (USB), fiber channel, Small Computer Systems Interface (SCSI), etc. The memory drives may further include a drum, magnetic disc drive, magneto-optical drive, optical drive, Redundant Array of Independent Discs (RAID), solid-state memory devices, solid-state drives, etc.

The memory 405 may store a collection of program or database components, including, without limitation, user interface application 406, an operating system 407, web server 408 etc. In some embodiments, computer system 400 may store user/application data 406, such as the data, variables, records, etc. as described in this invention. Such databases may be implemented as fault-tolerant, relational, scalable, secure databases such as Oracle or Sybase.

The operating system 407 may facilitate resource management and operation of the computer system 400. Examples of operating systems include, without limitation, Apple Macintosh OS X, UNIX, Unix-like system distributions (e.g., Berkeley Software Distribution (BSD), FreeBSD, NetBSD, OpenBSD, etc.), Linux distributions (e.g., Red Hat, Ubuntu, Kubuntu, etc.), International Business Machines (IBM) OS/2, Microsoft Windows (XP, Vista/7/8, etc.), Apple iOS, Google Android, Blackberry Operating System (OS), or the like. User interface 406 may facilitate display, execution, interaction, manipulation, or operation of program components through textual or graphical facilities. For example, user interfaces may provide computer interaction interface elements on a display system operatively connected to the computer system 400, such as cursors, icons, check boxes, menus, scrollers, windows, widgets, etc. Graphical User Interfaces (GUIs) may be employed, including, without limitation, Apple Macintosh operating systems' Aqua, IBM OS/2, Microsoft Windows (e.g., Aero, Metro, etc.), Unix X-Windows, web interface libraries (e.g., ActiveX, Java, Javascript, AJAX, HTML, Adobe Flash, etc.), or the like.

In some embodiments, the computer system 400 may implement a web browser 408 stored program component. The web browser may be a hypertext viewing application, such as Microsoft Internet Explorer, Google Chrome, Mozilla Firefox, Apple Safari, etc. Secure web browsing may be provided using Secure Hypertext Transport Protocol (HTTPS) secure sockets layer (SSL), Transport Layer Security (TLS), etc. Web browsers may utilize facilities such as AJAX, DHTML, Adobe Flash, JavaScript, Java, Application Programming Interfaces (APIs), etc. In some embodiments, the computer system 400 may implement a mail server stored program component. The mail server may be an Internet mail server such as Microsoft Exchange, or the like. The mail server may utilize facilities such as Active Server Pages (ASP), ActiveX, American National Standards Institute (ANSI) C++/C#, Microsoft .NET, CGI scripts, Java, JavaScript, PERL, PHP, Python, WebObjects, etc. The mail server may utilize communication protocols such as Internet Message Access Protocol (IMAP), Messaging Application Programming Interface (MAPI), Microsoft Exchange, Post Office Protocol (POP), Simple Mail Transfer Protocol (SMTP), or the like. In some embodiments, the computer system 400 may implement a mail client stored program component. The mail client may be a mail viewing application, such as Apple Mail, Microsoft Entourage, Microsoft Outlook, Mozilla Thunderbird, etc.

Furthermore, one or more computer-readable storage media may be utilized in implementing embodiments consistent with the present invention. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., non-transitory. Examples include Random Access Memory (RAM), Read-Only Memory (ROM), volatile memory, nonvolatile memory, hard drives, Compact Disc (CD) ROMs, Digital Video Disc (DVDs), flash drives, disks, and any other known physical storage media.

Advantages of the Embodiment of the Present Disclosure are Illustrated Herein

In an embodiment, the present disclosure provides real-time information about the operator's health condition or the condition of the infrastructure due to which the risks occurring due to operator's health, infrastructure characteristics can be avoided by taking immediate measures.

In an embodiment, the present disclosure provides a method wherein the operators may provide the status if the status detected by the mobile device is wrong and based on the operators input, the status is updated. By this, the mobile device learns and improves from past experiences of the actions of the operators corresponding to specific risk situations, thereby making the operating condition less prone to risks with time.

In an embodiment, the present disclosure provides a method wherein if the risk is exceeded due to the characteristics of the infrastructure the mobile device alerts the operator by giving a real-time feedback to take corrective actions/measures.

The terms "an embodiment", "embodiment", "embodiments", "the embodiment", "the embodiments", "one or more embodiments", "some embodiments", and "one embodiment" mean "one or more (but not all) embodiments of the invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise.

The terms "a", "an" and "the" mean "one or more", unless expressly specified otherwise.

A description of an embodiment with several components in communication with each other does not imply that all such components are required. On the contrary a variety of optional components are described to illustrate the wide variety of possible embodiments of the invention.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the embodiments of the present invention are intended to be illustrative, but not limiting, of the scope of the invention, which is set forth in the following claims.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

| Referral Numerals | |
|---|---|
| Reference Number | Description |
| 100 | Mobile Device |
| 101 | Interface |
| 103 | Memory |
| 105 | Processor |
| 107 | Operator Health Data |
| 109 | Environmental condition Data |
| 111 | Infrastructure operating data |
| 113 | Predefined Sensor Data |
| 115 | Other data |
| 117 | Receiving module |
| 119 | Operating condition detection module |
| 121 | Operating condition updating module |
| 125 | Output module |
| 127 | Other modules |
| 200 | Environment |
| 201 | Sensors |
| 202 | Client device |
| 203 | Communication network |
| 205 | Infrastructure monitoring server |

The invention claimed is:

1. A method for real-time monitoring of operating condition at an infrastructure, the method comprising:
   receiving, by one or more mobile devices associated with one or more operators of the infrastructure, data related to one or more monitoring parameters from each of one or more sensors;
   detecting, by the one or more mobile devices, status of the operating condition at the infrastructure based on the data, wherein the status is at least one of safe and unsafe, wherein the detected status is validated based on an input from the one or more operators, and wherein the input further comprises at least one monitoring parameter from the one or more monitoring parameters affecting the operating condition of the infrastructure;
   updating, by the one or more mobile devices, the status based on the input received on validity of the status from the one or more operators, wherein a predefined sensor value is updated by an infrastructure monitoring server based on the at least one monitoring parameter; and
   providing, by the one or more mobile devices, one or more measures associated with the one or more monitoring parameters based on the updated status thereby monitoring the operating condition at the infrastructure.

2. The method as claimed in claim 1, wherein updating the status comprises modifying the status as safe if the status is validated as safe by the one or more operators and modifying the status as unsafe if the status is validated as unsafe by the one or more operators.

3. The method as claimed in claim 1, wherein status information associated with the updated status is transmitted to an infrastructure monitoring server.

4. The method as claimed in claim 1 further comprises receiving input, from the one or more operators, on the one or more monitoring parameters affecting the operating condition at the infrastructure.

5. The method as claimed in claim 4, wherein the information associated with the input on the one or more operating parameters affecting the operating condition at the infrastructure is transmitted to the infrastructure monitoring server.

6. The method as claimed in claim 1, wherein the one or more sensors are configured at the infrastructure.

7. The method as claimed in claim 1, wherein detecting the status of the operating condition at the infrastructure comprises:
   obtaining a sensor value from the data;
   comparing the sensor value with the updated predefined sensor value;
   detecting the status of the operating condition to be safe if the sensor value is within the updated predefined sensor value; and
   detecting the status of the working condition to be unsafe if the sensor value exceeds the updated predefined sensor value.

8. The method as claimed in claim 1 further comprises providing a notification by the one or more mobile devices indicating the status of the operating condition.

9. A mobile device for real-time monitoring of operating condition at an infrastructure, the system comprising:
   a processor; and
   a memory communicatively coupled to the processor, wherein the memory stores processor-executable instructions, which, on execution, causes the processor to:
   receive data related to one or more monitoring parameters from each of one or more sensors;
   detect status of the operating condition at the infrastructure based on the data, wherein the status is at least one of safe and unsafe, wherein the detected status is validated based on an input from the one or more operators, and wherein the input further comprises at least one monitoring parameter from the one or more monitoring parameters affecting the operating condition of the infrastructure;
   update the status based on the input received on validity of the status from the one or more operators, wherein a predefined sensor value is updated by an infrastructure monitoring server based on the at least one monitoring parameter; and provide one or more measures associated with the one or more monitoring parameters based on the updated status thereby monitoring the operating condition at the infrastructure.

10. The mobile device as claimed in claim 9, wherein the processor updates the status of the operating condition by modifying the status as safe if the status is validated as safe by the one or more operators and modifying the status as unsafe if the status is validated as unsafe by the one or more operators.

11. The mobile device as claimed in claim 9, wherein the processor transmits the status information associated with the updated status to an infrastructure monitoring server.

12. The mobile device as claimed in claim 9 further comprises receiving, by the processor, input from the one or more operators on the one or more monitoring parameters affecting the operating condition at the infrastructure.

13. The mobile device as claimed in claim 12, wherein the processor transmits the information associated with the input on the one or more operating parameters to the infrastructure monitoring server.

14. The mobile device as claimed in claim 9, wherein the processor detects the status of the operating condition at the infrastructure by:

obtaining a sensor value from the data;
comparing the sensor value with the updated predefined sensor value;
detecting the status of the operating condition to be safe if the sensor value is within the updated predefined sensor value; and
detecting the status of the working condition to be unsafe if the sensor value exceeds the updated predefined sensor value.

15. The mobile device as claimed in claim 1 further comprises providing a notification by the one or more mobile devices indicating the status of the operating condition.

16. A non-transitory computer readable medium including instructions stored thereon that when processed by at least one processor cause a mobile device to perform operations comprising:

receiving data related to one or more monitoring parameters from each of one or more sensors;
detecting status of the operating condition at the infrastructure based on the data, wherein the status is at least one of safe and unsafe, wherein the detected status is validated based on an input from the one or more operators, and wherein the input further comprises at least one monitoring parameter from the one or more monitoring parameters affecting the operating condition of the infrastructure;
updating the status based on the input received on validity of the status from the one or more operators, wherein a predefined sensor value is updated by an infrastructure monitoring server based on the at least one monitoring parameter; and
providing one or more measures associated with the one or more monitoring parameters based on the updated status thereby monitoring the operating condition at the infrastructure.

17. The medium of claim 16, wherein the instructions further cause the at least one processor to update the status of the operating condition by modifying the status as safe if the status is validated as safe by the one or more operators and modifying the status as unsafe if the status is validated as unsafe by the one or more operators.

18. The medium of claim 16, wherein the instructions further cause the at least one processor to detect the status of the operating condition at the infrastructure by:

obtaining a sensor value from the data;
comparing the sensor value with the updated predefined sensor value;
detecting the status of the operating condition to be safe if the sensor value is within the updated predefined sensor value; and
detecting the status of the working condition to be unsafe if the sensor value exceeds the updated predefined sensor value.

* * * * *